United States Patent
Bolmsjö

Patent Number: 5,964,791
Date of Patent: Oct. 12, 1999

[54] APPARATUS FOR HEAT TREATMENT OF TISSUE

[75] Inventor: Magnus Bolmsjö, Lund, Sweden

[73] Assignee: ProstaLund Operations AB, Sweden

[21] Appl. No.: 08/952,260

[22] PCT Filed: May 17, 1996

[86] PCT No.: PCT/SE96/00649

§ 371 Date: Nov. 14, 1997

§ 102(e) Date: Nov. 14, 1997

[87] PCT Pub. No.: WO96/36288

PCT Pub. Date: Nov. 21, 1996

[30] Foreign Application Priority Data

May 18, 1995 [SE] Sweden ................................. 9501875

[51] Int. Cl.⁶ .................................................. A61B 17/39
[52] U.S. Cl. ........................... 607/100; 606/49; 607/102
[58] Field of Search .................................. 607/100–102, 607/122; 606/5, 15, 41, 49, 45

[56] References Cited

U.S. PATENT DOCUMENTS 5,222,953  6/1993  Dowlatshahi .
5,366,490  11/1994 Edwards et al. .
5,421,819  6/1995  Edwards et al. .

FOREIGN PATENT DOCUMENTS

0370890 A1  5/1990  European Pat. Off. .
0462302 A1  12/1991 European Pat. Off. .

Primary Examiner—Linda C. M. Dvorak
Assistant Examiner—Roy Gibson
Attorney, Agent, or Firm—Mathews, Collins, Shepherd & Gould, P.A.

[57] ABSTRACT

A device for heat treatment of body tissue, including heating means (10) for local heating of the body tissue, and temperature sensing means (11) for sensing the tissue temperature, said heating means being enclosed in a catheter (12). A first temperature sensing means (11) is connected to a first carrier (13), which is made to be advanced through a first opening in catheter (12), and said first carrier (13) is equipped with a pointed tip for insertion into such body tissue that is to be heat-treated.

15 Claims, 3 Drawing Sheets

APPARATUS FOR HEAT TREATMENT OF TISSUE

TECHNICAL FIELD OF THE INVENTION

The invention concerns a device for heat treatment of body tissue in accordance with patent claim 1.

Certain conditions of illness with unnatural growth of body tissue are successfully managed by the use of heat treatment. The tissue is heated to such an extent that the tissue dies. Certain types of cancer and hyperplasia in the prostate gland are examples of such conditions of illness. During treatment certain parts of the tissue are to be treated whereas others must or should be protected.

STATE OF THE ART

Various devices may be used for the purpose of producing heat. Laser as well as microwave and RF antennas are commonly used. Because the volume of the tissue to be treated varies, as does the heat-absorption quality of both this first-mentioned tissue and adjacent tissue, which is not to be treated, it is appropriate that continuous control takes place during treatment.

It is commonplace that the means of heating comprises some kind of a temperature sensor, which is provided on the heat-producing element to sense the temperature of an adjacent tissue. A drawback of this design is that the temperature sensor lends information that is more pertinent to the temperature of the element than to that of the tissue.

An example of this type of heating device is shown and described in EP 0 370 890. The device comprises a microwave antenna enclosed in a catheter. The antenna is designed to emit electromagnetic energy to the tissue surrounding the antenna. The catheter is also equipped with cooling channels for cooling of the tissue closest to the catheter. There is provided a temperature transducer in the catheter to sense the temperature of the catheter. The temperature sensed therefore does not agree with that of the tissue to be treated.

Another example of this is to be found in U.S. Pat. No. 5,366,490. According to that patent specification, previously known heating devices present multiple drawbacks. The most critical of these drawbacks is that heating takes place in a diffusely defined area or volume. In particular systems comprising a microwave antenna in a catheter, it is specified, lead to great risks and worse treatment outcome because the area of treatment is not narrowly defined.

According to U.S. Pat. No. 5,366,490, it is therefore suggested that the means of treatment is provided in a needle which is advanceable so as to exit a catheter. The catheter and then the needle are controlled very accurately in place with the aid of an ultra sound device, which during the entire treatment continuously monitors the area of treatment. Control of the needle must be very precise since treatment efficiency is locally very high in the vicinity of the needle. The treatment is a surgical one. There are high demands on the person who carries out the treatment and on the surgical equipment required.

SUMMARY OF THE INVENTION

It is an objective of the present invention, when it comes to conventional types of heat treatment devices, to provide a device which eliminates the drawbacks of diffusely working heating means that are equipped with temperature sensors. The objective is achieved by the features indicated in claim 1. According to the present invention, registration of relevant temperature data from the body tissue is readily made possible. Treatment made possible through the device according to the invention may take place in an outpatient setting without the requirement of surgical staff and equipment or operation rooms.

DESCRIPTION OF THE INVENTION

Figure 1:
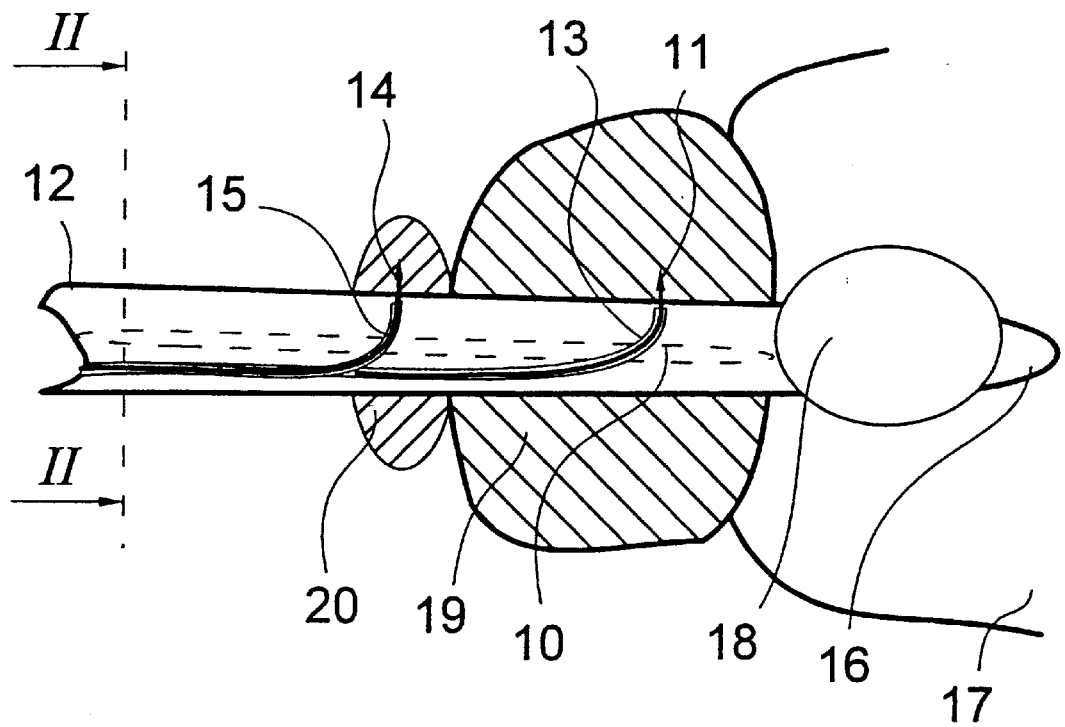
FIG. 1 is a side view partially in a cross-section of one embodiment of the device according to the invention.

In the embodiment schematically shown in FIG. 1, a catheter 12 has been inserted into the urethra in such a manner that a tip or apex 16 of catheter 12 has entered into the urine bladder 17. Prior to start of the treatment, a balloon 18 connected to catheter 12 is expanded inside the urine bladder. Unintentional extraction of the catheter 12 is thereby prevented. An external sphincter 20 schematically indicates such surrounding tissue which is not to undergo treatment.

Catheter 12 comprises means 10 for heating tissue in the prostate gland 19. In a preferred embodiment, the heating device 10 comprises an antenna for emission of electromagnetic energy. The antenna usually operates within the frequency range of 1 MHz–5000 MHz. In other embodiments, the heating device 10 comprises receptacles containing, a heated liquid. The heating may take place through circulation of the heated liquid through catheter 12, or through some form of a heating element in a direct connection to the receptacle. It is also possible to have the heating device 10 abut either directly to the tissue or indirectly via an intermediary device. The intermediary device may be so designed that it expands during heating, thus allowing for an improved abutment against the tissue, and improved heat transmission as well.

In yet other embodiments, the heating device 10 may comprise one or several smaller radio frequency electrodes provided externally on the catheter. A larger electrode interacts with the catheter electrode in such a way that it is heated by the transmitted radio energy.

An active portion of the heating device 10 is located in the prostate gland 19. Supply of the energy, which is to be emitted to the tissue, preferably occurs in channels in catheter 12. Below, these will be described in more detail with reference to FIG. 2.

In the course of an ongoing treatment the tissue is heated. Heating should occur within certain temperature intervals for the sake of optimal treatment results. If the temperature is too elevated, unnecessary severe damage is inflicted on the tissue. If the temperature is too low, on the other hand, the desired treatment result is not achieved. In order to be directly able to register temperature increase in the tissue to be treated a first temperature sensing means 11 is connected to a first carrier 13. Carrier 13 is run through a channel in catheter 12 and is provided so as to be advanced through an opening in catheter 12. Preferably, there is provided a guide for carrier 13 in the opening of the catheter, so as to guide carrier 13 out and into the tissue at a desired angle relative to catheter 12. Carrier 13 may also run in a tubing in the catheter. The guide includes a sloping or inclined portion, against which the carrier 13 can be brought and, thus, be angled out and, upon further advancement, moved away from the catheter. The carrier 13 is constructed of a relatively stiff material, thus facilitating penetration and insertion into the tissue.

Either carrier 13 or temperature sensing means 11 is equipped with a tip, which allows for a more simplified insertion into the tissue. Temperature sensing means 11 may be either conventionally designed as a resistive transducer or a semi-conductor. The cable drawing required for such transducers is preferably carried out through catheter 12. If an optical type of transducer is used, a fiber optic conductor is provided through catheter 12.

Advancement of the temperature sensing means 11 or its carrier 13 out of catheter 12 is controlled by control means from the exterior of the catheter outside of the body. This should preferably occur in a well defined way so that insertion into the tissue is implemented down to the desired depth. In a simple design, carrier 13 is made as a stiff tube ending in a tip and is provided to extend through a channel in catheter 12. Temperature sensing means 11 is provided at one end of carrier 13. At the other end, carrier 13 is equipped with a handle. The channel and carrier 13, which is contained in the channel, are given such dimensions and such a bending resistance that the degree of advancement becomes well defined in relation to the longitudinal advancement of the carrier. The advancement by maneuvering of the handle and carrier is limited by a stop or some arresting means so as to avoid the risk of the temperature sensing means 11 passing beyond the desired area of temperature sensing.

By continuously sensing of the temperature in the tissue being treated, it is possible to accurately control supplied power and the end result. Thus, the risk of undesired damage to the tissue is significantly diminished.

In order to further lessen the risk of damage, and more specifically in such surrounding tissue which shall not be reached through treatment, a second temperature sensing means 14 is connected to a second carrier 15. This second carrier 15 is designed to be advanced through and out of catheter 12 at a certain distance from the first carrier 13 in the longitudinal direction of the catheter 12. The distance is determined by the size of the treatment area and is ample enough to allow temperature sensing means 14, in its forwardly advanced state, to penetrate into such a tissue which should not be damaged during treatment. In the shown embodiment the second temperature sensing means 14 measures the temperature in the sphincter 20.

Figure 2:
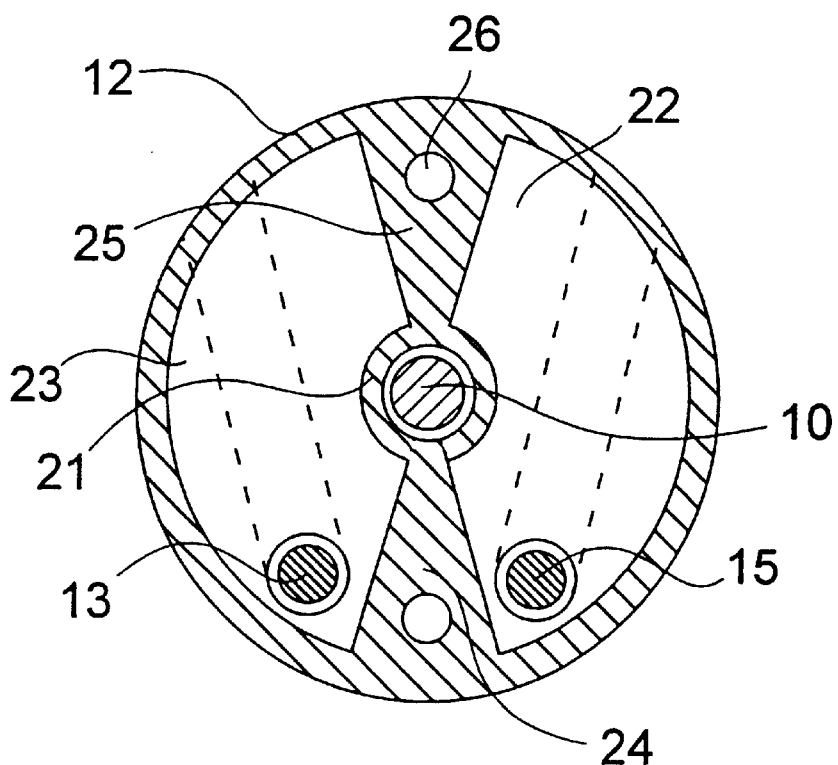
FIG. 2 is a cross-sectional view from line II—II of FIG. 1.

The cross-section view of FIG. 2 shows an example of how catheter 12 may be designed. The heating device 10 and its conductor for energy supply are contained in a centrally provided, first channel or tube 21. Tube 21 is surrounded by two radially displaced, communicating cavities 22, 23. Through these cavities there is distributed a cooling medium or coolant for cooling the tissue in direct contiguity to the heating device 10 in such applications for which heat treatment is directed towards the tissue at a certain radial distance from the heating device 10 and catheter 12. This is specifically applicable in cases when the heating device 10 includes an antenna.

The cooling medium is mainly used to avoid heating of tissue surrounding the catheter on its way to the treatment area, and which would be due to heat loss or similar from the conductor of the heating device 10.

Different portions of the catheter periphery are joined by two portions 24, 25, in which there are provided elongate channels 26 to allow for inflation and deflation of balloon 18. Portions 24, 25 merge into the central tube 21.

Figure 3:
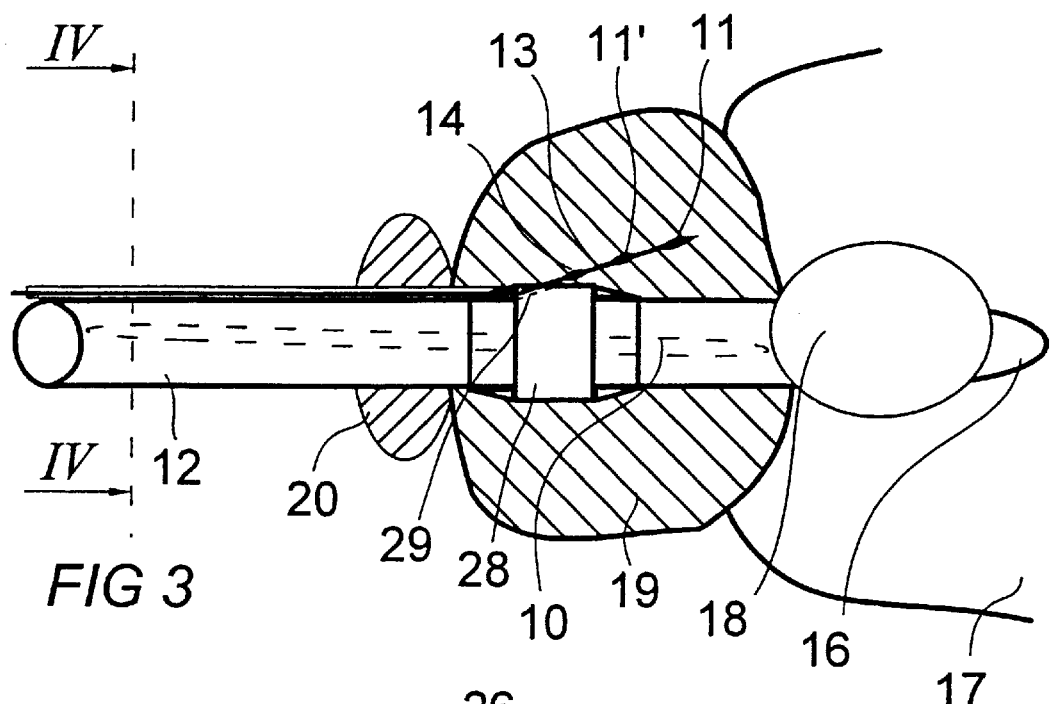
FIG. 3 is a principal longitudinal view of a practical embodiment of a device according to the invention.

In the practical embodiment of the device according to the invention, shown in FIG. 3, a tubing 27 made of Teflon or a similar material is provided external to the catheter. Tubing 27 is connected to a sleeve 28 mounted on catheter 12. Sleeve 28, in a portion outside of the orifice of tubing 27, is provided with an inclined portion 29. Preferably the sleeve is arranged with relation to the heating device 10 in such a way that the sleeve, in its operative mode, is located in the periphery or outside of the working area of heating device 10.

The annular member 20 also has a stiffening effect, which prevents undesirable downward bending of catheter 12 in conjunction with forward push advancement of carrier 13. The length of annular member 20 is adjusted to retain the suppleness and pliability of catheter 12.

Carrier 13, which is equipped with one or several temperature sensing means 11; 14, extends through tubing 27. Carrier 13 is rigid and has a pointed end. When the carrier is pushed in and passed through tubing 27 and reaching the inclined portion 29, which is preferably composed of a relatively hard material, carrier 13 is bent into a certain angle projecting out from the longitudinal direction of catheter 12. An advantageous angle has to be at least approximately 20°. A preferred angle is 30°. During continued insertion of carrier 13, its pointed end tip will penetrate the tissue outside of sleeve 28, and will penetrate further into the tissue as forward advancement continues. Selection of materials for carrier 13 and tubing 27 is done so that friction between them becomes suitably low.

As shown by FIG. 3, carrier 13 is equipped with several temperature transducers. These are arranged with a distance between them. A first temperature transducer 11 is provided at the pointed end tip of carrier 13, and a second temperature transducer 14 is provided at a distance from the pointed end tip corresponding to a normal distance of advancement by push of the carrier out of sleeve 28. Thereby this second temperature transducer 14 will be located in the periphery or outside of the area of treatment. There is provided an additional temperature transducer 11' between the two abovementioned temperature transducers 11;14. In the normal operative mode this third temperature transducer 11' is located in the middle of the area of treatment.

Figure 4:
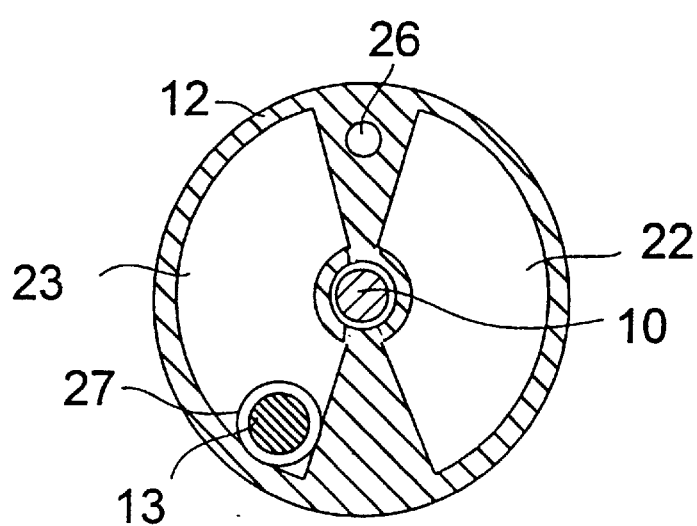
FIG. 4 is a cross-sectional view, from line IV—IV of FIG. 3, of an alternate embodiment of a device according to the invention.
Figure 5:
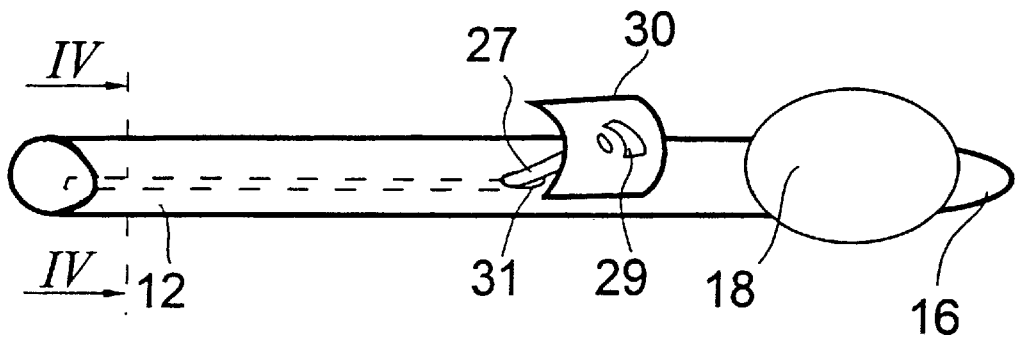
FIG. 5 is a principal longitudinal view of an alternate, practical embodiment of a device according to the invention, during assembly.

In the embodiment as per FIGS. 4 and 5, tubing 27 is arranged to run internally in catheter 12, most preferably within one of the channels 22 or 23. Tubing 27 at one end is attached to an end piece, which like sleeve 28 comprises a sloping or inclined portion 29. End piece 30 constitutes part of catheter 12, or is joined to catheter 12 so that the inclined portion 29 is located outside of an opening 31 made in catheter 12. Tubing 27 runs through this opening 31. During manufacture of a catheter according to this embodiment it is suitable that tubing 27 is led into the opening 31 from the outside and then led back through the catheter and out through an open end of the catheter. There is indication about such a procedure in FIG. 5, wherein end piece 30 has not yet been fastened to the exterior of catheter 12. Some materials used for tubing 27 must have a mechanical connection, for instance clamping, of the tubing against or onto end piece 30. Upon connection, tubing 27 should exhibit such a direction that a carrier, which is pushed out through the orifice of tubing 27, hits the inclined portion 29 and is outwardly directed at a desirable angle.

The end piece 30 and the orifice of tubing 27 are preferably covered by a diaphragm or a membrane. This allows for simple sterilization and cleaning of catheter 12 prior to usage. Upon insertion of catheter 12 into the treatment position, the diaphragm will be penetrated by carrier 13 in conjunction with the forward advancement of the carrier and temperature sensing means. In one embodiment, end piece 30 is provided as a supple plate, which covers part of the circumference of catheter 12.

For some applications it may prove insufficient with two temperature sensing means. Several elongate cavities for carriers and related sensing means will then be provided in the catheter. The heating device could also be provided in several separated elements. These could be arranged in multiple tubes or channels as well.

Figure 6:
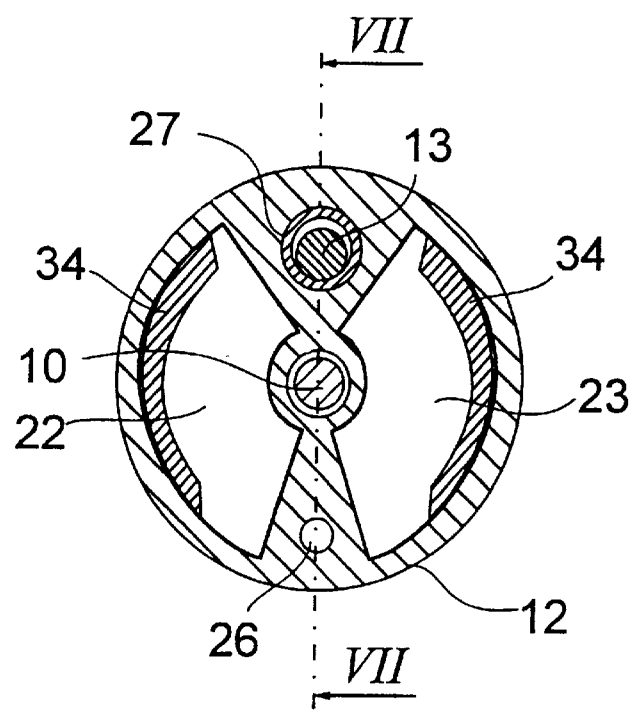
FIG. 6 is a cross-sectional view, from line VI—VI in FIG. 7, of yet another alternate embodiment of a device according to the invention.

In the embodiment as per FIG. 6, tubing 27 is provided in a special cavity of catheter 12. Tubing 27 runs through virtually the entire catheter 12. A peg 32 (see FIG. 7) is inserted into tubing 27 from the end facing the tip 16. Peg 32 is an end member in the tubing and is provided with an oblique, pointed end face 33, which has the same function as the inclined portion 29 in the embodiments described above. If stiffening of catheter 12 is required in this embodiment, one or several stiffening members 34 are preferably provided in catheter 12, so that catheter 12 obtains a completely smooth exterior. Advantageously, the stiffening members 34 are arranged in channels 22 and 23, as shown in FIG. 6.

Figure 7:
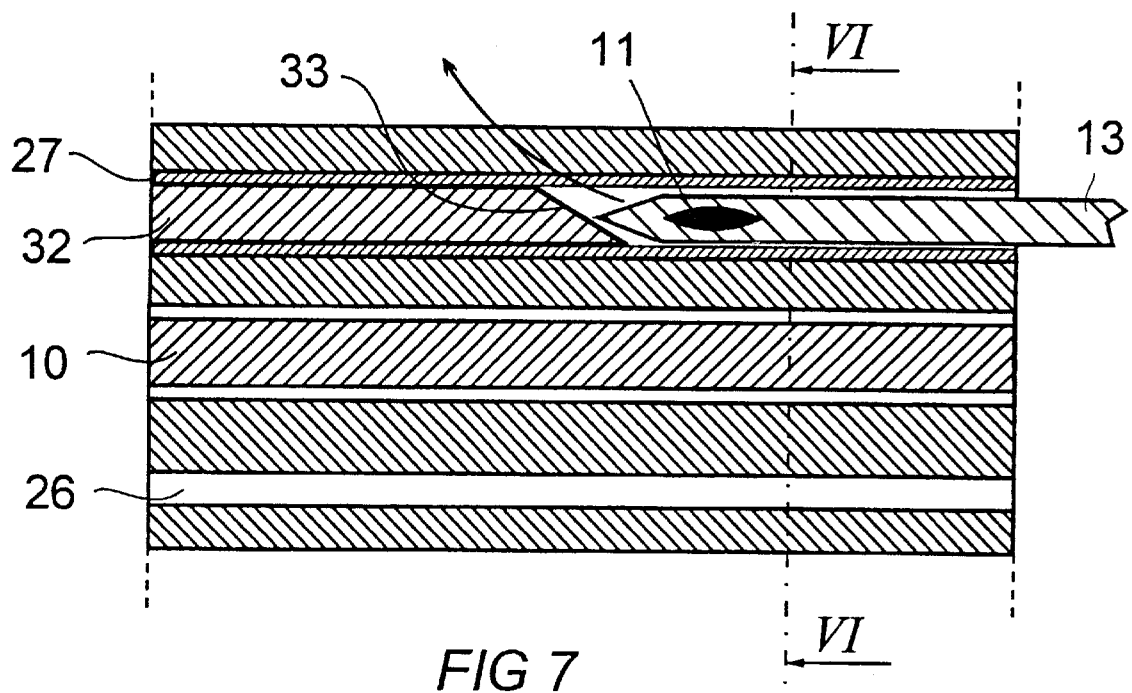
FIG. 7 is a longitudinal partial view, taken from line VII—VII, of the device of FIG. 8.

In FIG. 7, only part of catheter 12 is shown as designed in accordance with FIG. 6. Carrier 13 has been introduced into tubing 27 unto a position in which the pointed end tip engages the pointed end face of peg 32. As in the embodiments described above, carrier 13 upon further insertion of tubing 27 will be forced to deviate from an axial direction and adopt a deflected angle determined by the inclination of the sloping portion 29, which in this embodiment is represented by the pointed end face of peg 32. Carrier 13, in the shown embodiment, penetrates both the tubing 27 and the wall of catheter 12. In other embodiments, catheter 12 may be provided with a weakened portion in the area which is to be penetrated. It is also possible to make an opening, in advance, in catheter 12 and/or in tubing 27. The opening is preferably covered by a membrane or similar during insertion into the urethra or equivalent.

The increased resistance, which appears during deflection against the inclined portion 29 or pointed end face 33, can be used to define a starting point from which to determine the depth of insertion into the tissue, of carrier 13 with its pointed tip and temperature sensing means 11. This depth is also determined by the deflection angle. The signals generated at least by the first temperature sensing means 11 are conducted to an indicator unit, by means of which the attending staff can continuously assess the treatment. Preferably, the signals are also sent to a control unit not detailed herein, and which controls supply of power to the heating device 10. In the case of multiple temperature sensing means being used, it would be preferable to connect them to the indicator unit and/or control unit.

I claim:

1. A device for heat treatment of prostate tissue comprising:

heating means for local heating of the prostate tissue;

a urological catheter enclosing said heating means; and a first temperature sensing means connected to a first carrier, said first carrier for sensing the temperature of the prostate tissue being movable through radially and out a wall of said catheter and said first carrier having a first end forming a first pointed tip, wherein said first pointed tip being adapted for insertion into the prostate tissue that is to be heat treated and that is located radially of said urological catheter.

2. The device according to claim 1 further comprising:

a second temperature sensing means connected to a second carrier, said second carrier being movable through and out of said catheter and said second carrier having a first end formed with a second pointed tip, wherein said second tip being adapted for insertion into prostate tissue which is to be excluded from said heat treatment.

3. The device according to claim 1, wherein said first carrier is contained in cavities in said catheter.

4. The device according to claim 1 wherein said first carrier is contained in a tubing located on said catheter.

5. The device according to claim 4 wherein said tubing debouches into an end piece, said end piece having an inclined portion for angulation of said first carrier.

6. The device according to claim 5 wherein said end piece is provided externally on said catheter and said end piece is made of a material that is more rigid than said catheter so as to avoid undesired kinking of said catheter.

7. The device according to claim 5 wherein said end piece is provided internally in said catheter.

8. The device according to claim 7 further comprising:

at least one stiffening member positioned internally in said catheter.

9. The device according to claim 1 wherein said heating means comprises at least one microwave antenna for delivery of energy to the body tissue.

10. The device according to claim 9 further comprising:

at least one heat-absorbing means in the vicinity of said microwave antenna for dissipation of heat from prostate tissue closest to said antenna.

11. The device according to claim 10 wherein said at least one heat-absorbing means comprises channels which extend through said catheter and a cooling medium being distributed through said channels.

12. The device according to claim 11 wherein stiffening means is positioned in said channels in said catheter.

13. The device according to claim 1 wherein at least one heat-absorbing means is provided for dissipation of heat from the prostate tissue closes to a supply lead connected to said heating means.

14. The device according to claim 1 wherein said temperature sensing means is connected to a control unit, said control unit controlling the power of said heating means.

15. A method for heat treatment of prostate tissue, comprising the steps of:

local heating of the prostate tissue with at least one heating means, said heating means being enclosed in a catheter;

continuously sensing of the prostate tissue temperature with a temperature sensing means; and advancing said temperature sensing means which is connected with a first carrier through and radially out of said catheter and into the prostate tissue which is to be treated and is located radially external to said catheter for continuous control of the tissue temperature.

* * * * *

UNITED STATES PATENT AND TRADEMARK OFFICE
CERTIFICATE OF CORRECTION

PATENT NO.   : 5,964,791
DATED        : October 12, 1999
INVENTOR(S)  : Magnus Bolmsjo It is certified that error appears in the above-identified patent and that said Letters Patent is hereby corrected as shown below:

Column 5,
Line 49, insert -- with a longitudinal axis and completely -- after "urological catheter"
Line 53, delete "radially and" and insert therefor -- and radially --
Line 54, insert -- directed radially to said longitudinal axis, -- after "catheter"

Column 6,
Line 48, insert -- completely -- after "being"
Line 49, insert -- with a longitudinal axis -- after "catheter"
Line 54, insert -- directed radially to said longitudinal axis, -- after "catheter"

Signed and Sealed this

Seventh Day of June, 2005

JON W. DUDAS
*Director of the United States Patent and Trademark Office*